United States Patent [19]

Simard

[11] Patent Number: 5,476,592
[45] Date of Patent: Dec. 19, 1995

[54] METHOD AND DEVICE FOR INJECTION OF A STERILE AND ANTIPYROGENIC FLUID

[75] Inventor: Laurent Simard, Lyons, France

[73] Assignee: Hospal Industrie, France

[21] Appl. No.: 233,790

[22] Filed: Apr. 26, 1994

[30] Foreign Application Priority Data

Apr. 27, 1993 [FR] France .................................. 93 05190

[51] Int. Cl.[6] .................................................. B01D 61/32
[52] U.S. Cl. .............................. 210/651; 210/90; 210/93; 210/321.69; 210/636; 210/646; 210/739
[58] Field of Search ........................ 210/90, 93, 321.69, 210/335, 636, 646, 739, 741, 742, 929, 650, 651

[56] References Cited

U.S. PATENT DOCUMENTS

| | | | |
|---|---|---|---|
| 2,860,784 | 11/1958 | Breithaupt | 210/93 |
| 4,107,037 | 8/1978 | Cavanaugh et al. | 210/90 |
| 4,191,182 | 3/1980 | Popovich et al. | 210/90 |
| 4,702,829 | 10/1987 | Polaschegg et al. | 210/195.2 |
| 4,708,802 | 11/1987 | Rath et al. | 210/641 |
| 4,834,888 | 5/1989 | Polaschegg | 210/321.69 |
| 5,024,756 | 6/1991 | Sternby | 210/93 |
| 5,069,792 | 12/1991 | Prince et al. | 210/627 |
| 5,108,612 | 4/1992 | Flaig et al. | 210/90 |
| 5,152,895 | 10/1992 | Doucet | 210/90 |
| 5,185,078 | 2/1993 | Koczy | 210/93 |

FOREIGN PATENT DOCUMENTS

| | | | |
|---|---|---|---|
| 0212127A1 | 3/1987 | European Pat. Off. | |
| 3110022 | 10/1982 | Germany | 210/93 |
| WO91/05576 | 5/1991 | WIPO | |

*Primary Examiner*—Joseph W. Drodge
*Attorney, Agent, or Firm*—Finnegan, Henderson, Farabow, Garrett & Dunner

[57] ABSTRACT

A device and method for injecting a sterile pyrogen free fluid uses a main filter having first and second compartments separated by a porous membrane. The first compartment has an inlet connected to a source of fluid to be filtered, and the second compartment has an outlet connected to an injection line. A pump is provided for circulating the fluid through the main filter and into the injection line. A secondary filter is provided downstream of the main filter and, in combination with pressure sensors, is used to determine if a rupture exists in the main filter.

17 Claims, 1 Drawing Sheet

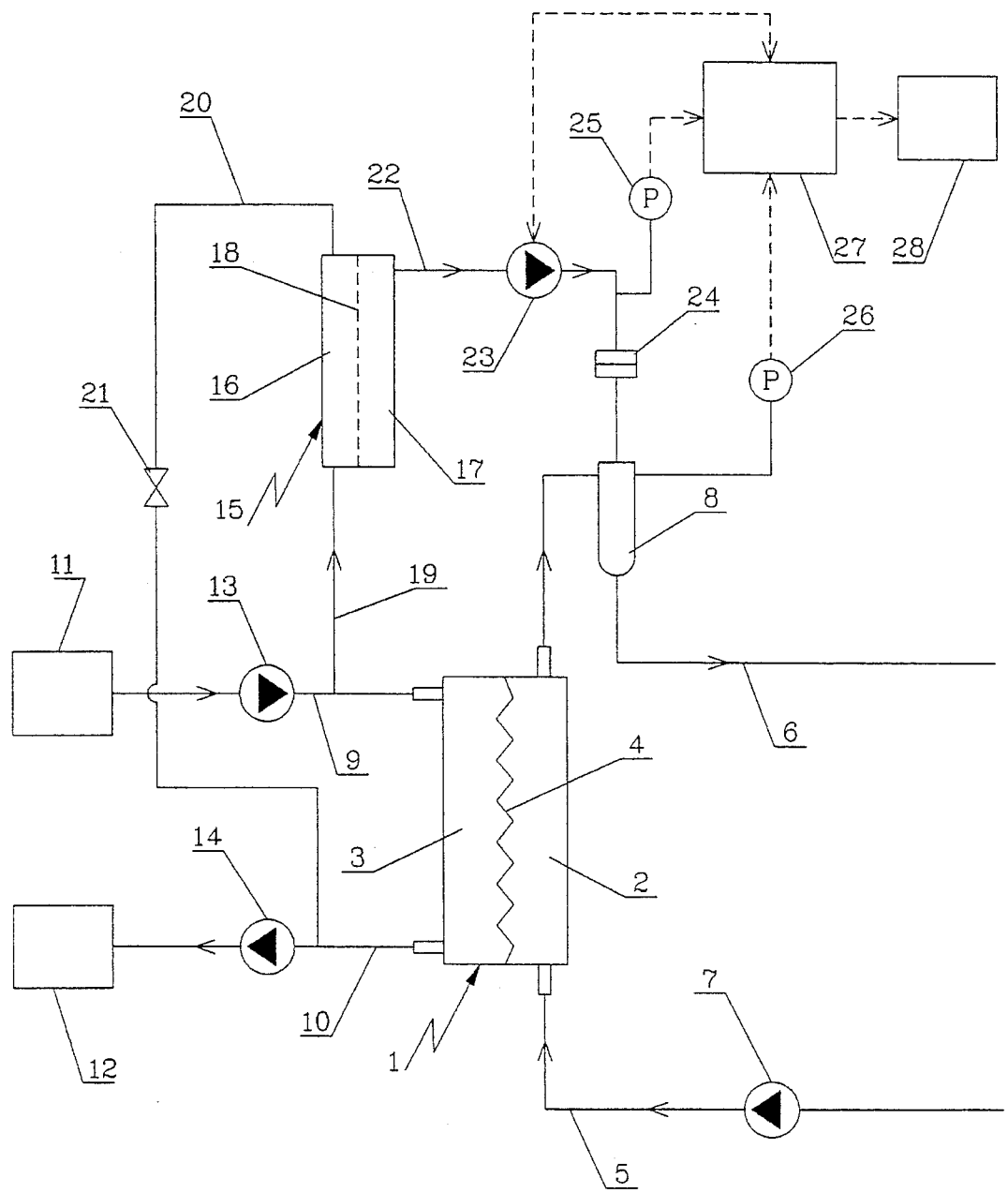

METHOD AND DEVICE FOR INJECTION OF A STERILE AND ANTIPYROGENIC FLUID

BACKGROUND OF THE INVENTION

1. Field of the Invention

The present invention relates to a device for injection of a sterile and antipyrogenic fluid obtained by filtration, and to a method for checking the integrity of the filter used for this purpose.

2. Description of the Related Art

The injection device according to the invention is of the type that includes: at least one filter having a first and a second compartment which are separated by a porous membrane, the first compartment having an inlet which can be connected to a source of fluid to be filtered, and the second compartment having an outlet connected to an injection channel; means for circulating the fluid through the filter and into the injection channel; and means for checking the integrity of the filter.

Such a device is described in the patent U.S. Pat. No. 4,702,829, in combination with a haemodiafiltration installation. In this device, the first compartment of a first filter is equipped with a vent insulated from the atmosphere by a hydrophobic microfilter, and it is connected, by way of a second filter, to a supply channel of a dialysis circuit. During operation, the injection channel is connected to a bubble trap of a purified blood return channel which is linked to a patient.

The integrity of the filters is checked outside the operating periods of the installation. To do this, the dialyser is removed from the dialysis fluid circuit, and the dialysis fluid circuit is linked up in such a way as to form a closed circuit. Also, the injection channel is connected to the dialysis fluid circuit. Dialysis fluid is then pumped from the dialysis fluid circuit, whereby air enters through the vent of the first filter into the compartments of the filters which are in communication. Dialysis fluid is pumped until the compartments of the filters which are in communication are filled with air and until a defined subpressure is created in the circuit. The pressure in the circuit is measured: if the membranes are intact, air can not pass through them and the pressure remains constant.

This method for checking the integrity of the filters has the disadvantage that it can only be used outside the treatment sessions. Furthermore, it requires the use of a particular filter having a first compartment equipped with a vent insulated from the atmosphere by a hydrophobic microfilter.

The object of the invention is to provide an injection device of the type mentioned above, the filter of which can be checked during use.

SUMMARY OF THE INVENTION

To achieve this object, means for checking the integrity of the filter are proposed according to the invention, these means comprising:

a secondary filter which is able to hold back bacteria and pyrogens and is arranged on the injection channel, and means for detecting a clogging of the secondary filter during the injection of fluid.

According to one characteristic of the invention, the means for detecting a clogging of the secondary filter comprise:

means for measuring a difference in the pressures existing on each side of the secondary filter, and means for comparing the difference in the pressures measured with a threshold value, and, if appropriate, means for emitting an alarm when the difference in the pressures measured reaches a threshold value.

The invention also relates to a method for checking the integrity of a main filter used to render sterile and antipyrogenic a fluid intended to be injected continuously to a patient, the main filter having a first and a second compartment which are separated by a porous membrane, and the first compartment having an inlet which can be connected to a source of fluid to be filtered, and the second compartment having an outlet connected to an injection channel, the method comprising the steps of:

placing a secondary filter on the injection channel, and measuring in the injection channel, during the injection, the value of a parameter susceptible of being influenced by a clogging of the secondary filter, such as the difference in the pressures existing on each side of the secondary filter.

According to one characteristic of the invention, the method additionally comprises the step of comparing the measured value of the parameter with a threshold value. The threshold value can be chosen, for example, as a function of the flow rate or the temperature of the injection fluid or of these two characteristics. For example, the threshold value can also be chosen substantially equal to the value of the parameter measured at the start of the injection of the fluid.

According to another characteristic of the invention, the method additionally comprises the step of emitting an alarm or stopping the injection when the measured value of the parameter reaches a threshold value.

Other characteristics and advantages of the invention will emerge from reading the description which follows. Reference will be made to the attached figure which represents the simplified outline of a haemodiafiltration installation comprising the injection device according to the invention.

BRIEF DESCRIPTION OF THE DRAWING

FIG. 1 is a schematic diagram of a haemodiafiltration installation in accordance with the present invention.

DESCRIPTION OF THE PREFERRED EMBODIMENT

The haemofiltration installation represented in the figure comprises an exchanger or haemodiafilter 1 divided into two compartments 2, 5 by a semi-permeable membrane 4 permitting the dialysis and ultrafiltration of blood. The compartment 2 constitutes a portion of an extracorporeal blood circuit comprising a withdrawal channel 5 intended to convey the blood from the patient (not shown) to the haemodiafilter 1, as well as a return channel 6 intended to convey the treated blood from the haemodiafilter 1 to the patient. The withdrawal channel 5 is equipped with a circulation pump 7. The return channel 6 is equipped with a bubble trap 8.

The compartment 3 is intended for the circulation of a dialysis fluid. This compartment has an inlet connected, via a supply channel 9 equipped with a first circulation pump 13, to a generator 11 of dialysis fluid. The compartment 3 has an outlet connected, via a removal channel 10 equipped with a second circulation pump 14, to a removal element 12 for spent fluid.

The haemodiafiltration installation which has just been described is equipped with a device for injection of sterile and antipyrogenic fluid obtained by filtration of the dialysis fluid. This device comprises a main filter 15 having a first and a second compartment 16, 17 which are separated by a porous membrane 18 able to hold back the bacterial and pyrogenic elements of the dialysis fluid. The first compartment 16 has an inlet connected to the dialysis fluid supply channel 9 via a channel 19 which is connected to the supply channel 9 between the first pump 13 and the haemodiafilter 1. The first compartment 16 has an outlet connected to the dialysis fluid removal channel 10 via a channel 20 which is connected to the removal channel 10 between the haemodiafilter 1 and the second circulation pump 14. Arranged on the channel 20 is a valve 21, the periodic opening of which permits cleaning of the membrane 18 by tangential sweeping of the surface of the membrane by means of the unfiltered fluid.

The second compartment 17 of the main filter 15 has an outlet connected, via an injection channel 22, to the bubble trap 8 of the return channel 6 of the extracorporeal blood circuit. A circulation pump 23 is arranged on the injection channel 22.

In accordance with the invention, the injection device comprises means which make it possible to check the integrity of the main filter 15 during the haemodiafiltration session. These checking means comprise a secondary filter 24 which is able to hold back the bacteria and the pyrogenic elements and which is arranged on the injection channel between the injection pump 23 and the bubble trap 8, and two pressure sensors 25, 26 which are connected to the injection line 22 on each side of the secondary filter 24. The signals from the two pressure sensors 25, 26 are supplied to a control unit 27 which calculates, either continuously or periodically, a differential pressure value and compares it to a threshold value. If the membrane 18 of the main filter 15 is damaged initially, or if it bursts during use of the filter, bacteria and pyrogenic elements will pass into the injection line 22 and will be stopped by the secondary filter 24. This clogging will result in an increase in the difference of the pressures on each side of the secondary filter 24. When this difference reaches the threshold value which has previously been fixed, the control unit triggers alarm means 28 and effects the stoppage of the pump 23. The emission of the alarm and the stoppage of the injection pump 23 can also be effected at two different threshold values.

The secondary filter 24 has a membrane whose porosity is less than approximately 0.45 μm and is preferably between approximately 20 μm and approximately 24 μm. The surface of the membrane is chosen as a function of the injection flow rate which can be between approximately 1 and approximately 50 milliliters per minute. It is a matter of the secondary filter 24 not causing too great a loss of head in the injection line and at the same time offering a membrane surface which is sufficiently reduced to ensure that a rupture of the main filter 15 results in a rapid clogging of the secondary filter 24.

By way of example, for a flow rate of the order of 1 milliliter per minute, it is possible to use a filter of 13 millimeters in diameter, and for a flow rate of approximately 20 milliliters per minute, it is possible to use a filter of 25 millimeters in diameter (Millex GV filters, manufactured by the company Millipore, the hydrophilic membrane of PVDF having a porosity of 0.22 μm).

For a given filter size, the threshold value mentioned above is chosen as a function of the flow rate of the fluid and, if appropriate, of its temperature, that is to say also of its viscosity. By way of example, it is possible to adopt, as threshold value, the difference in the pressures existing on each side of the secondary filter when the injection starts.

The functioning of the device thus described is as follows. After connecting the patient to the extracorporeal blood circuit, the pump 7 is set in operation, and the blood withdrawn continuously from the patient circulates in the haemodiafilter 1 in contact with the membrane 4. The dialysis fluid, prepared by the dialysis fluid generator 11, is set in circulation in the channels 9, 10 and the compartment 3 of the haemodiafilter 1 by means of the pumps 13, 14. Inside the haemodiafilter 1, exchanges take place across the semi-permeable membrane 4 between the blood and the dialysis fluid. These exchanges are due in the first instance to the phenomenon of diffusion resulting from the difference between the concentrations of the solutes in the blood and the dialysis fluid, the dialysis fluid being free in particular of the substances from which it is desired to purify the blood (urea, creatinine). In addition, exchanges are due to the phenomenon of convection caused by the difference in pressure created on each side of the membrane. Conditions for circulation of the blood and of the dialysis fluid are chosen in a conventional manner in such a way that the pressure in the blood compartment is greater than the pressure in the dialysis fluid compartment. Thus, a fraction of plasmatic fluid passes by ultrafiltration across the membrane 18, which permits better purification of the blood.

The required pressure conditions for effecting ultrafiltration of the blood can be obtained by causing the pumps 13 and 14 for circulation of the dialysis fluid to turn at the same rate, and by causing the injection device to function. The injection pump 23 effecting aspiration in the dialysis fluid circuit brings about the desired partial vacuum therein. Under these operating conditions, the ultrafiltered plasmatic fluid is replaced by a similar quantity of replacement fluid injected into the patient.

The dialysis fluid aspirated in the channel 9 by the injection pump 23 is filtered by passing across the membrane 18 of the main filter 15. The membrane 18 holds back the bacteria and the pyrogenic elements of the dialysis fluid which can then be injected into the extracorporeal blood circuit. Before its injection into the blood, the replacement fluid passes through the secondary filter 24 which, in addition to its specific function, described above, as an element in the means for checking the integrity of the main filter, also constitutes an important safety member in the event of rupture of the main filter 15, insofar as it prevents the injection of bacterial and pyrogenic elements into the patient.

According to the invention, such an incident will be detected by virtue of the information issuing from the pressure sensors 25 and 26. Indeed, in the event of a defect in the integrity of the main filter 15, the undesirable elements not held back by this filter will be stopped by the secondary filter 24 which, given its reduced surface area, will have a tendency rapidly to become blocked. A clogging of the secondary filter 24 will result, if the output of the injection pump 18 is maintained constant, in an increase in the difference between the pressures existing on each side of the secondary filter 24.

During the haemodiafiltration session, the pressure sensors 25 and 26 supply, to the control unit 27, signals corresponding to the instantaneous pressure values. The control unit 27 calculates the difference in the pressures and compares it to the threshold value previously fixed and stored. If the difference in the pressures reaches the threshold value, the control unit 27 triggers the alarm means 28. The control unit 27 can additionally effect the stoppage of the injection pump 23. As mentioned above, it is possible to choose two different threshold values: a first value corresponding to a slight clogging of the secondary filter 24 and serving as reference for the triggering of the alarm; and a second threshold value corresponding to a more substantial clogging of the secondary filter 24 and serving as reference for effecting the stoppage of the injection pump 23.

It is also possible, instead of comparing the instantaneous values of the difference in the pressures to the threshold value, to form an average, over a certain period, of the values of the difference in the pressures and to compare the mean value obtained to the threshold value. This makes it possible to take into account the variations in pressure which would be due, not to a clogging of the secondary filter 24, but to the functioning of the injection pump 23.

Since the difference in the pressures on each side of the microfilter depends on the flow rate provided by the injection pump 23, it is desirable to change the threshold value when the flow rate of the injection pump 23 changes. This can be achieved by supplying the control unit 27 with the relationship existing between the threshold value and the flow rate of the pump 23. Thus, the control unit 27, subsequently receiving the information relating to the flow rate of the pump 23, will be able to modify the threshold value as a function of the changes in the flow rate of the pump.

As mentioned above, with the mode of functioning which has just been described the quantity of plasmatic fluid withdrawn from the patient by ultrafiltration is compensated by an equal quantity of replacement fluid injected into the extracorporeal blood circuit. It is often desirable to have the patient lose weight, that is to say to withdraw more plasmatic fluid than there is replacement fluid injected. In this case it suffices to regulate the dialysis fluid pump 14 situated downstream of the haemodiafilter 1 in such a way that its flow rate is greater than the flow rate of the dialysis fluid pump 13 situated upstream of the haemodiafilter 1. The difference between the two flow rates will be equal to the rate of weight loss.

The invention is not limited to the embodiment which has just been described. In particular, it should be clear that although the injection device according to the invention has been described in combination with a haemodiafiltration installation, this device can be used in a totally independent manner. Instead of being a dialysis fluid prepared by a dialysis fluid generator, the fluid used will be prepared, for example, by metered mixing of water and concentrated solutions containing the desired electrolytes and, if appropriate, the desired proteins.

What is claimed is:

1. A device for injection of a sterile and pyrogen free fluid, comprising:
    at least one main filter having a first compartment and a second compartment separated by a porous membrane, the membrane having a filtration surface, the first compartment having an inlet for connection to a source of fluid to be filtered, and the second compartment having an outlet connected to an injection line;
    means for circulating the fluid through the at least one main filter and into the injection line; and
    means for checking the integrity of the at least one main filter, the checking means including a secondary filter which is able to hold back bacteria and pyrogens and is arranged in the injection line so that all the fluid filtered through the at least one main filter passes through the secondary filter, the secondary filter having a filtration surface which is substantially smaller than the filtration surface of the at least one main filter, and the checking means further including means for detecting a clogging of the secondary filter during an injection of fluid via the injector line to determine if a rupture exists in the at least one main filter.

2. A device according to claim 1, wherein the means for detecting a clogging of the secondary filter includes means for measuring a difference in pressure existing on each side of the secondary filter and means for comparing the difference in pressure measured with a threshold value.

3. A device according to claim 2, further including means for emitting an alarm when the measured pressure difference reaches the threshold value.

4. A device according to claim 2, wherein the secondary filter has a porosity of less than approximately 0.45 μm.

5. Injection device according to claim 4, wherein the secondary filter has a porosity of between approximately 0.20 μm and approximately 0.24 μm.

6. A device according to claim 1, wherein the source of fluid is a dialysis fluid generator.

7. A device according to claim 1, wherein the injection line is connectable to an extracorporeal blood circuit.

8. A device according to claim 1, wherein the first compartment of the at least one main filter has an outlet connectable to a removal line in order to permit membrane cleaning during an injection procedure, by directing fluid to be filtered tangentially to the membrane through the first compartment.

9. A device according to claim 16 further including means for stopping the circulating means in response to detection of clogging in the secondary filter by the detecting means.

10. A device according to claim 16 further including means for notifying an operator in response to detection of clogging of the secondary filter by the detecting means.

11. A method for checking the integrity of a main filter used to render sterile and pyrogen free a fluid intended for continuous injection, the main filter having a first compartment and a second compartment separated from the first compartment by a porous membrane, the first compartment having an inlet connectable to a source of fluid to be filtered, and the second compartment having an outlet connected to an injection line, the method comprising the steps of:
    flowing all fluid filtered by the main filter through the secondary filter, the secondary filter being able to hold back bacteria and pyrogens and having a membrane with a filtration surface which is substantially smaller than the filtration surface of the membrane of the main filter;
    measuring in the injection line during fluid injection, a value of a parameter susceptible to being influenced by a clogging of the secondary filter; and
    determining the integrity of the main filter based on the measured value.

12. Method according to claim 11, wherein the parameter is the difference in the pressures existing on each side of the secondary filter (24).

13. Method according to claim 11, additionally comprising the step of comparing the measured value of the parameter with a threshold value.

14. Method according to claim 13, wherein the threshold value is chosen as a function of at least one characteristic of the injection fluid including flow rate and temperature.

15. Method according to claim 13, wherein the threshold value is chosen substantially equal to the value of the parameter measured at the start of the injection of the fluid.

16. Method according to claims 13, additionally comprising the step of emitting an alarm when the measured value of the parameter reaches a threshold value.

17. Method according to claim 13, additionally comprising the step of stopping the injection when the measured value of the parameter reaches a threshold value.

* * * * *

UNITED STATES PATENT AND TRADEMARK OFFICE
CERTIFICATE OF CORRECTION

PATENT NO. : 5,476,592
DATED : December 19, 1995
INVENTOR(S) : Laurent SIMARD

It is certified that error appears in the above-indentified patent and that said Letters Patent is hereby corrected as shown below:

Claim 5, column 6, line 20, "Injection" should read --A--.

Claim 9, column 6, line 35, "claim 16" should read --claim 1--.

Claim 10, column 6, line 38, "claim 16" should read --claim 1--.

Claim 16, column 7, line 7, "claims 13" should read --claim 13--.

Signed and Sealed this

Twenty-third Day of April, 1996

Attest:

BRUCE LEHMAN

*Attesting Officer*  Commissioner of Patents and Trademarks